United States Patent [19]
Tonoyan et al.

[11] Patent Number: 5,533,208
[45] Date of Patent: Jul. 9, 1996

[54] FOLDING ADJUSTABLE GLASSES ON CAP PEAK

[76] Inventors: Lily Tonoyan; Karen Minasian, both of 1600 Taft Ave., Apt. 506, Los Angeles, Calif. 90028

[21] Appl. No.: 442,679

[22] Filed: May 17, 1995

[51] Int. Cl.⁶ ........................................................ A42B 1/06
[52] U.S. Cl. ................... 2/10; 2/209.13; 2/453; 351/155
[58] Field of Search ..................... 2/10, 12, 13, 209.13, 2/453, 6.3, 6.5, 6.7; 351/155

[56] References Cited

U.S. PATENT DOCUMENTS

| | | | |
|---|---|---|---|
| 2,725,560 | 12/1955 | Feldman | 2/10 |
| 4,951,316 | 8/1990 | Moody | 351/155 |
| 5,208,916 | 5/1993 | Kelman | 351/155 |
| 5,261,124 | 11/1993 | Day | 2/10 |

*Primary Examiner*—Diana Biefeld
*Attorney, Agent, or Firm*—Curt Harrington

[57] ABSTRACT

An eye wear visor includes a visor structure which is provided which can engage the user's head about the upper portion above the user's ears, and is preferably made of durable plastic. The visor has a downwardly sloped forward brim surface which supports a guide rail having a "C" shaped axial cross section which is downwardly disposed and which engages a cylindrical portion of an attachment member. The attachment member can be displaced along the rail and has an opening having a laterally oriented axis, the opening having a hexagonal shape and supports a main hexagonal support. The main hexagonal support individually and independently supports a right and a left lens assembly via hexagonal bores in each of the right and left lens assemblies. The hexagonal and laterally sliding relationship provides continuous adjustment of the spacing between the lens assemblies to accomodate a wide variety of users whose eye spacing and location can vary with respect to the traditional support structures on the human head used to support eye wear.

12 Claims, 4 Drawing Sheets

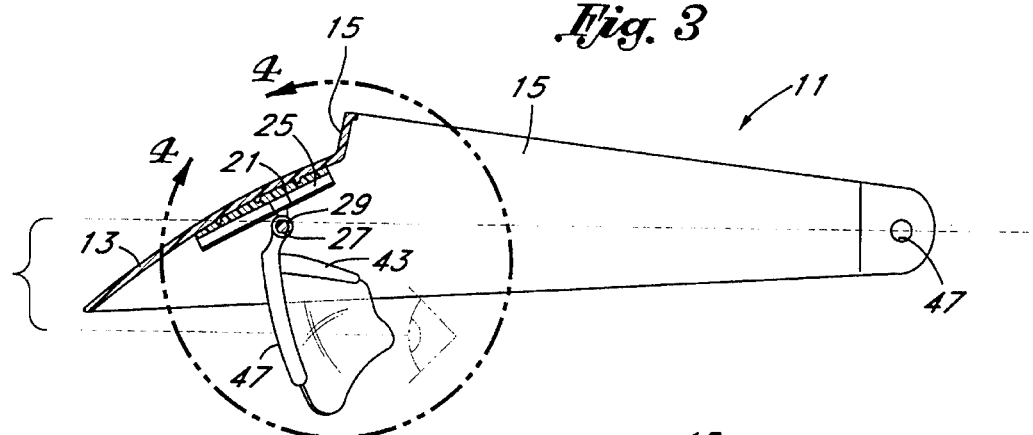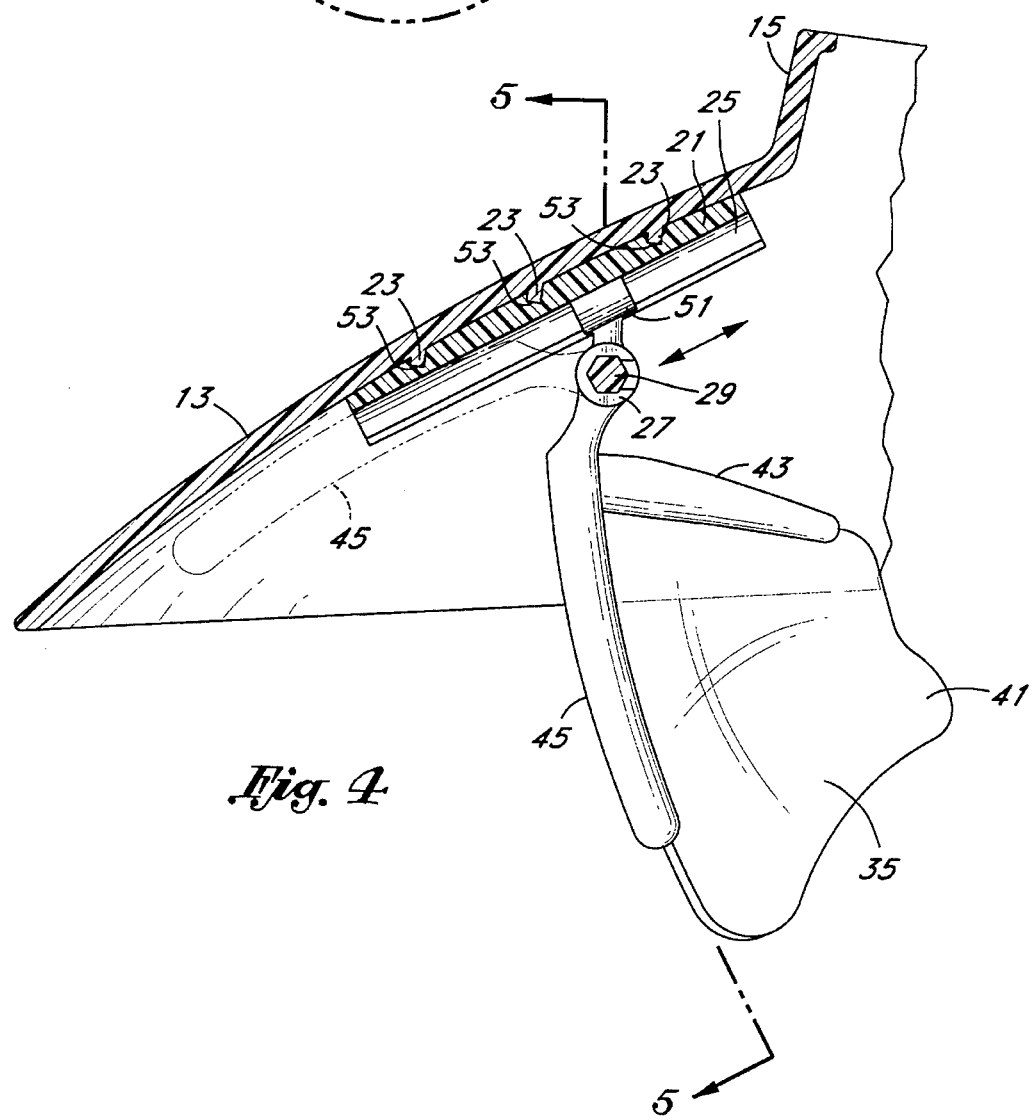

FOLDING ADJUSTABLE GLASSES ON CAP PEAK

FIELD OF THE INVENTION

The present invention relates to the field of eye wear. More specifically, the present invention relates to a device and method for providing efficient and stable eye wear on a person and having a number of utilitarian features built into the design thereof which lends great flexability and benefits to the user.

BACKGROUND OF THE INVENTION

It is generally uncomfortable for a user to wear glasses and sun glasses. It is often even more uncomfortable to combine the wearing of glasses with the simultaneous wear of other head gear, especially caps and hats. The eye wear ear pieces can interfere with the proper fitting and wearing of a hat or visor. In some cases the hat or visor will compress the ear pieces against the head which can cause sorness and damage to the user's scalp.

Further complicating the use of glasses and sun glasses and the like are the wearing of such items combined with various types of activities. When biking or swimming, a complicated set of structures worn on the head can be especially unworkable or uncomfortable. Sweat can invade the area between the eye wear lens and eyes and spoil the view. In some cases conventional eye wear can block the flow of air from circulation around the eye wear which will exaccerbate the problem of sweating.

In conventional eye wear, all of the factors which make for comfort, will generally entail a close fit. A closer fit helps more evenly cover the eyes to block out direct sunlight entering from the sides. Closeness of fit not only spreads the contact surfaces between the eye wear and the face, but also brings the eye wear closer to the face. This problem makes worse the sweating problem discussed above. In the case of an individual who has had an operation, such as facial plastic surgery, the ability to wear normal eye wear may be precluded altogether due to the bearing of such conventional eye wear on the face.

SUMMARY OF THE INVENTION

A visor structure is provided which can engage the user's head about the upper portion above the user's ears, and is preferably made of durable plastic. The visor has a downwardly sloped forward brim surface which supports a guide rail on the underside of the sloped brim surface. The guide rail has a "C" shaped axial cross section which is downwardly disposed and which engages a cylindrical portion of an attachment member. The attachment member has an opening having a laterally oriented axis, the opening having a hexagonal shape. The opening of the attachment member supports a main hexagonal support, preferably from the center of the main hexagonal support.

The main hexagonal support individually and independently supports a right and a left lens assembly via hexagonal bores in each of the right and left lens assemblies. The hexagonal and laterally sliding relationship provides continuous adjustment of the spacing between the lens assemblies to accomodate a wide variety of users whose eye spacing and location can vary with respect to the traditional support structures on the human head used to support eye wear.

For example, a user with sensitive areas of facial tissue or whose eye positioning is not centered with respect to the nose location can adjust the eye wear of the present invention freely since the support is had with a visor which is supported by the upper portion of the head and which eye wear is suspended from a point above and forward of the eyes.

The right and left lens assemblies can be laterally moved along or removed from the main hexagonal support. If removed from the main hexagonal suppport, the lenses and lens supports can be replaced on the hexagonal support tilted 60° upwardly to thus be carried and yet angularly displace from in front of the user's eyes.

The combination of these motions with the presence of the guide rail on the underside of the sloped brim surface gives the eye wear visor of the present invention even further flexibility. Because the brim surface is sloped, the guide rail is similarly sloped, and the lens assemblies as they are supported from the main hexagonal support can be moved forward and downwardly away from the user's eyes, or rearwardly and upwardly toward the user's eyes. The forward and downward position is advantageous in reading, while the rearward and upward position is advantageous for being near and protecting the user's eyes, such as from the wind. The upper and rear position also more completely surrounds the users eyes, particularly with the extended area lenses.

Since the attachment member has a rotationally fixed attachment with respect to the main hexagonal support and the hexagonal support has a rotationally fixed relationship with respect to the lens support assemblies, the lens support assemblies are not freely rotatable with respect to the visor portion of the eye wear visor. However, since the attachment member has an open orientation, an impact to the lens support assemblies can cause the lens supports, including the hexagonal support to snap free of the attachment member, to minimize any injury to the wearer.

BRIEF DESCRIPTION OF THE DRAWINGS

The invention, its configuration, construction, and operation will be best further described in the following detailed description, taken in conjunction with the accompanying drawings in which:

FIG. 3 is a side sectional view taken along line 3—3 of FIG. 2 and illustrating the details of suspension of the lens structures with respect to the visor;

FIG. 4 is an expanded view of the cross section of FIG. 3 and illustrating the details of the lens structure, especially the angular slidability of the support and the angular locking of the angle assumed by the lens structure;

FIG. 7 is a side exploded view of the eye wear of the present invention.

DETAILED DESCRIPTION OF THE PREFERRED EMBODIMENT

Figure 1:
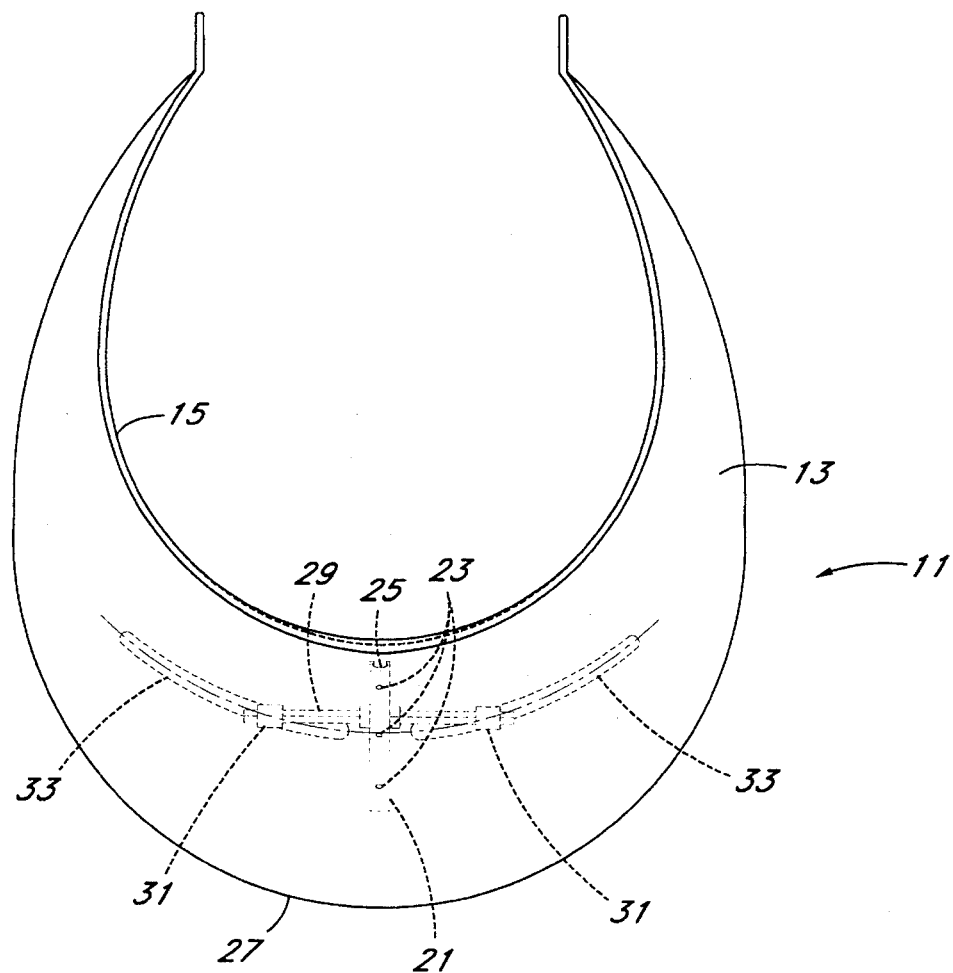
FIG. 1 is a top view of the eye wear device of the present invention and illustrating the optical and support structures in phantom.

The description and operation of the invention will be best described with reference to FIG. 1. FIG. 1 is an eye wear visor 11, inlcuding sloping brim surface 13. Eye wear visor 11 has a vertical portion 15 which will fit against the user's head, and may or may not include a thin layer of soft sponge or deformable material to oppose the surface of the user's head.

Shown in phamtom near the middle of the sloping brim surface 13 is an attachment rail 21 having a series of three circular apertures 23. The attachment rail 21 has a downwardly directed "C" channel 25, the cross sectional shape of which is somewhat revealed at the end of the projection. Also shown is an attachment member 27 which is slidably displaceable with respect to the attachment rail 21 and which supports all the structures lying to the left and right of the attachment rail 21.

A main hexagonal support 29 is directly attached to the attachment member 27 and is bilaterally centered with respect to the eye wear visor 11, and extend laterally. As can also be seen, are round lateral engagement members 31, each of which is a portion of the lens support structures 33, all of which are shown in phamtom. The lateral engagement members 31 are frictionally laterally slidable with respect to the hexagonal support 29 to move the lens support structures 33 laterally closer to and farther from the attachment rail 21.

The attachment member 27 has a partially open extent which will both engage the main hexagonal support 29, yet allow the main hexagonal support 29 to pop free of the attachment member if the eye wear portion of the eye wear visor 11 is accidentally struck. By providing this escape, an accidental blow to either the visor portion or the eye wear portion of the eye wear visor 11 will not transmit force to the user through the other structure.

This provides adjustment of the space between lenses which will be shown and which will thus accommodate users with closely set and with widely set eyes. This adjustment is a fine adjustment in terms of absolute distance, but is critical in ensuring a good fit for a wide variety of users.

Figure 2:
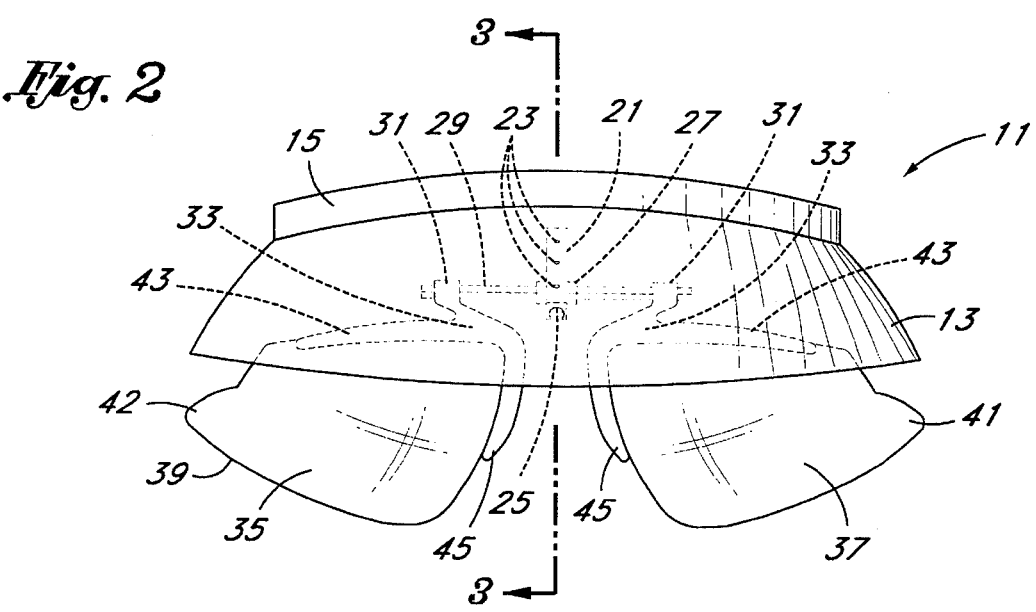
FIG. 2 is a front view of the device of FIG. 2 and where the optical and support structures are shown partially in phantom.

Referring to FIG. 2, a front view of the eye wear 11 of the present invention reveals a set of lenses, including a right lens 35 and a left lens 37 taken with respect to the orientation of the wearer. With respect to the right lens 35, note the unusual shape. The lower edge 39 sweeps significant rearwardly and laterally away from the attachment rail 21. The lower edge 39 ends in an acutely angled area 41 having a rounded apex. The same is true for the left lens 37 which similarly terminates in an angled area 41.

As can also be seen in FIG. 2, each of the lens support structures 33 extend over the right and left lenses 35 and 37 in a generally horizontal fashion with a horizontal portion 43, and extend downwardly around the right and left lenses 35 and 37 in a generally vertical fashion with a vertical portion 45. The horizontal portions 43 and the vertical portions 45 engage their lenses 35 and 37 by the use of a lock mechanism to be shown later, rather than by simple interfit or gluing.

With regard to motion, FIG. 2 illustrates that motion of the attachment member 27 along the attachment rail 21 as translating into some vertical displacement of the hexagonal support 29 as well as the right and left lens 35 and 37. Note the way in which the right and left lenses 35 and 37, from the vertical portions 45, sweep broadly in the lateral direction and then gently upwardly toward the angled area 41 in a form which somewhat conforms to the human face, but significantly lower than the extent of conventional eye wear. Where most eye wear attempts to block light by virtue of closeness of the eye wear to the face, the visor eye wear 11 of the present invention provides lenses 35 and 37 of extended area which are adjustable to cover the vision area of the user.

Referring to FIG. 3, a sectional view taken along line 3—3 of FIG. 2 divides the attachment rail 21 about its center and shows half of the "C"0 shaped channel 25. An aperture 47 is shown at the rear of the eye wear visor 11 to secure string or an elastic or other member to support the visor 11 either on a user's head or for hanging on a structure when not in use.

Referring to FIG. 4, an enlarged view taken about line 4—4 of FIG. 3 illustrates an extreme closeup of the area encircled by line 4—4 of FIG. 3. A cylindrical member 51 is more explicitly shown within the "C" shaped channel 25 of attachment rail 21, and is the structure about which the "C" shaped channel 25 grasps and which is allowed to frictionally move with such "C" shaped channel 25. Also more clearly seen are the three circular apertures 23 which are shown as filled with plugs 53 of material from the sloping brim surface 13 of the visor 11.

Figure 5:
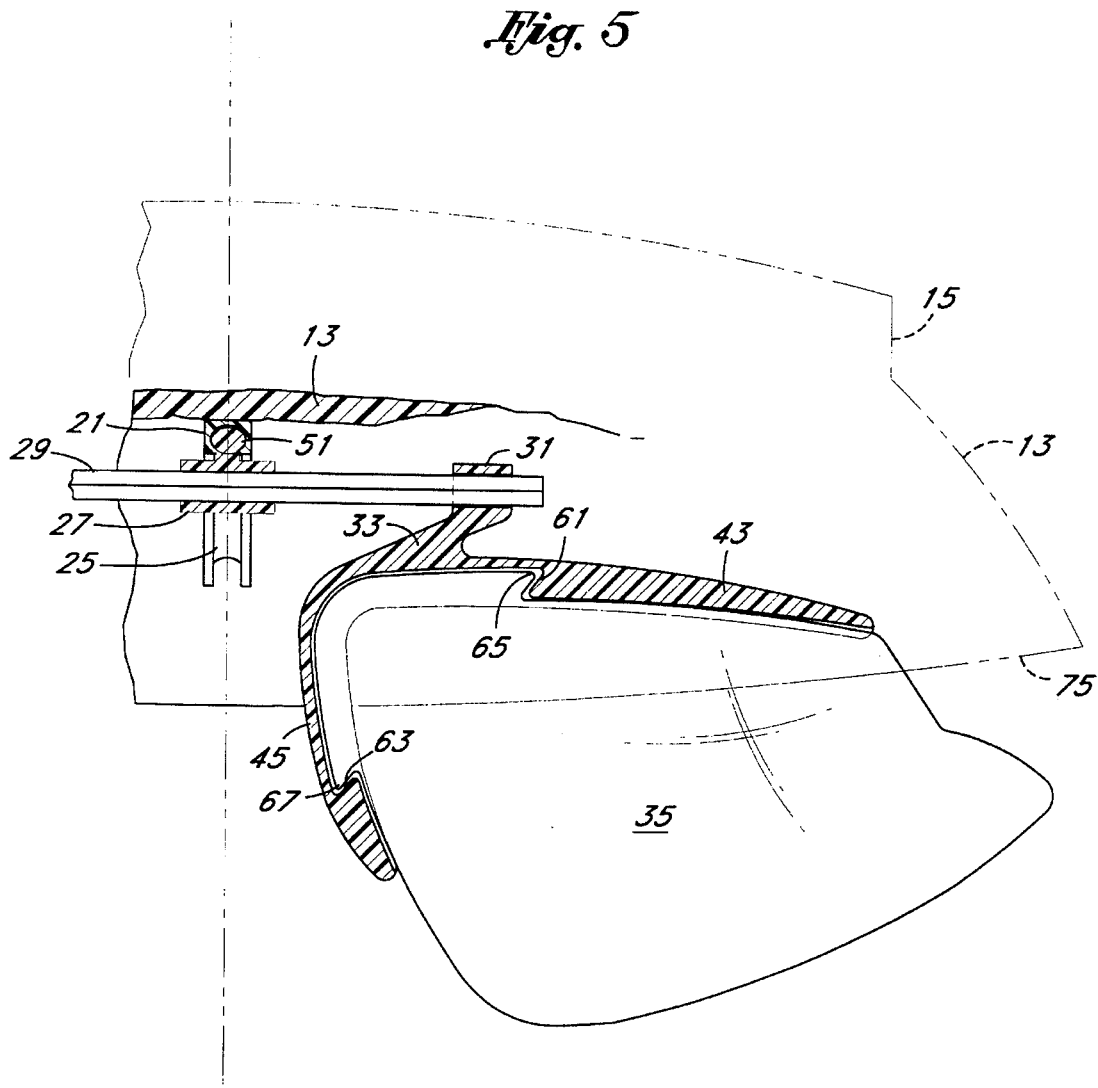
FIG. 5 is a sectional view taken along curved line 5—5 of FIG. 4 and illustrating the manner in which the support structures interact with the lens material and with the slidable support.
Figure 2:
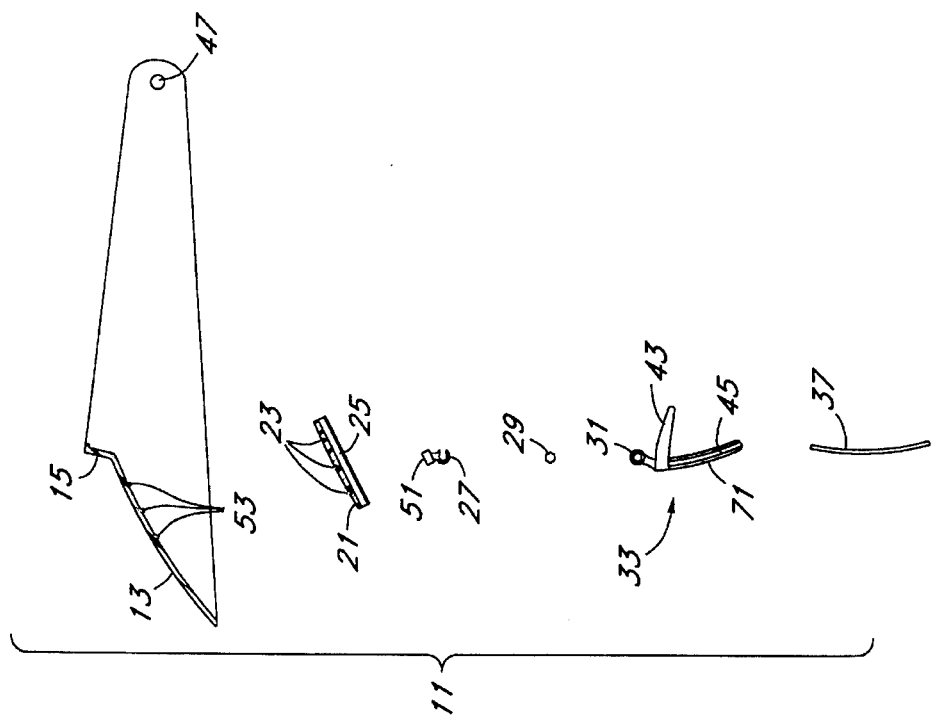

Referring to FIG. 5, a sectional view taken along line 5—5 of FIG. 4 illustrates the holding mechanics of several structures thereof. The horizontal portion 43 defines an "S" shaped interlock 61 while the vertical portion 45 defines a similar "S" shaped interlock 63. The right lens 35 also has an "S" shaped interlock 65 which interfits with an "S" shaped interlock 63, and it has an "S" shaped interlock 67 which interfits with the "S" shaped interlock 63.

The complementary interlocks 61 and 65, and complementary interlocks 63 and 67 enable the lenses 35 and 37 to be locked into their respective lens support structures 33. The lens support structures 33, including the horizontal portions 43 and vertical portion 45 can be provided as a single piece structure or a pair of opposing structures along a plane generally described by the line 5—5.

The angularity of the complementary interlocks 61 and 65, and complementary interlocks 63 and 67 can provide varying degrees of positive locked interfit. As the severity of the angularity of these structures are increased, manufacture may depend more upon machine insertion and provide a greater interlock. A lesser severity of angularity may provide for user interchangeability of lenses 35 and 37, by reducing the force necessary to insert and remove the lenses 35 and 37.

FIG. 5 also shows the details of the attachment member 27 and how it engages the main hexagonal support member 29. Also shown is the cylindrical member 51 and the somewhat oval section cut therethrough in accord to the section line shown in FIG. 4. The engagement of the cylindrical member 51 by both the attachment member 27 and the round lateral engagement members 31 is positive with respect to preventing angular displacement between the attachment rail 21 and the round lateral engagement members 31.

The round lateral engagement members 31 have hexagonal internal surfaces which engage the hexagonal outer portion of main hexagonal support 29 and prevent angular displacement of the lens support structures 33 with respect to the main hexagonal support 29. Likewise, the internal surfaces of the attachment member 27 are hexagonal and engage the hexagonal outer portion of main hexagonal support 29 and prevent angular displacement of the main hexagonal support 29 with respect to the attachment member 27. In this way, angular displacement between the attachment rail 21 and the round lateral engagement members 31 is prevented.

Note however that the lens support structures 33 can be laterally and frictionally displaced along the hexagonal support 29 for disengagement from the hexagonal support 29. Since a hexagonal support has six even sides, the lens support structure 33 can be replaced onto the support in a different position which is one sixth of a circle in angular difference. This 360°/6 or 60° displacement can be performed by removing each of the lens support structures 33 from the left and right ends of the hexagonal support 29 and replacing the lens support structures 33 angularly displaced about the axial length of the hexagonal support 29 outwardly to fold against the underside of the sloping brim surface 13.

In this way, the eye wear visor 11 can be worn with the left and right lenses 35 and 37 folded up and away from the face. Further, and because the lens support structures 33 can still be moved along the attachment rail 21, a portion of the lower edge of the right and left lens can be made to protrude from under a lower edge 75 of the sloping brim surface 13, to provide extended partial shading to the user's face. Note that the attachment rail 21 can be made longer or shorter, to enable the lens support structures 33 and left and right lenses to move even further down and beyond the lower edge 75 of the brim surface 13.

The attachment rail 21 may or may not be fitted with stops to limit the movement of the lens support structures along the attachment rail 21 and especially downwardly toward the edge 75 of the sloping brim surface 13. So long as one end of the attachment rail 21 is left open, the attachment member 27 may be completely removed from the attachment rail 21 to completely remove all of the eye wear structures supported by the attachment member 27 from the visor structure made up of sloping brim surface 13 and vertical portion 15. These structures include attachment member 27, main hexagonal support 29, round lateral engagement members 31, lens support structures 33, right lens 35, and left lens 37.

Thus, the eye wear visor 11 of the present invention lends itself to three distinct modes of use, two of which are completely adjustable. With the eye wear structures removed, the eye wear visor 11 of the present becomes simply a visor. With the eye wear structures in the upper position, as indicated by the dashed line showing in FIG. 4, the eye wear structures are present and may be adjusted to provide additional shading. With the eye wear structures in the lowered position, as indicated by the showing in FIG. 3, the eye wear structures are present to protect the eyes of the user and may be adjusted to provide closeness to and distance from the eyes. For Example, for reading it may be desirable to bring the eye wear structures far from the user's face to cut glare from a book, but to increase the peripheral non-shaded vision. For biking, it may be desirable to bring the eye wear structures close to the face to protect the eyes from flowing wind.

Figure 6:
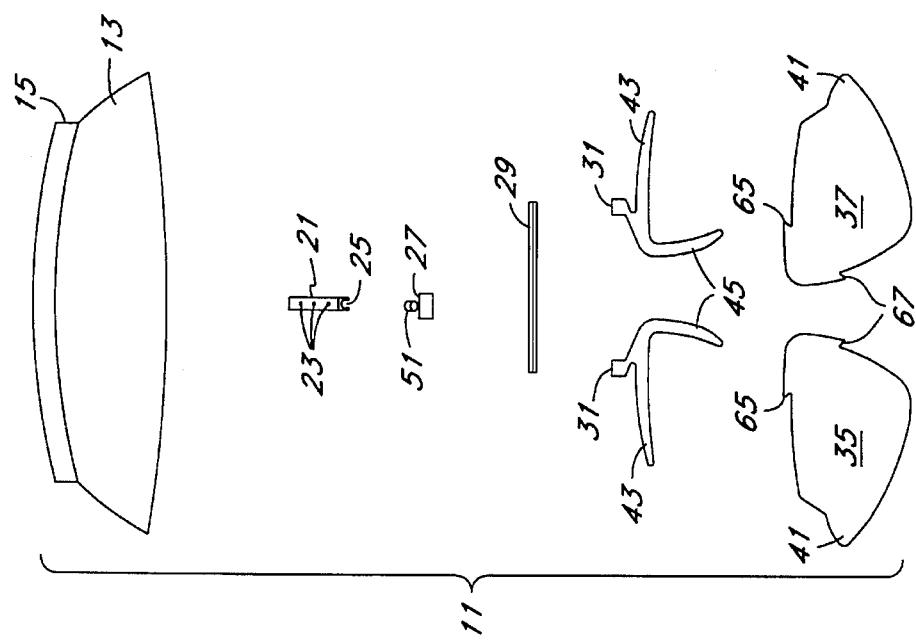
FIG. 6 is a front exploded view of the eye wear of the present invention.

Referring to FIG. 6, an exploded view is shown in which the exploded members are viewed from a frontal orientation. The relationship of the structures associated with the attachment member 27 are more readily seen, as are all of the other structures.

Referring to FIG. 7, an exploded view in partial section from the left illustrates further details of the eye wear visor 11 of the present invention. The plugs 53 which extend down from the sloping brim surface 13 are seen as they are when not being engaged into the circular apertures 23 of the attachment rail 21.

The cupped, open sided nature of the portion of the attachment member 27 which receives the main hexagonal support 29 is also shown, as is the cylindrical member 51. However, the lens support structure 33 shown is the left structure which illustrates a slot 71 on the vertical portion 45. The left lens 37 is also shown.

While the present invention has been described in terms of a eye wear visor 11, one skilled in the art will realize that the structure and techniques of the present invention can be applied to many appliances. The present invention may be applied in any situation where remote support, combined with enhanced adjustability in eye wear is desired.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. An eye wear visor comprising:

a visor structure including a brim surface having an underside;

an attachment rail attached to said underside of said visor structure and further comprising a "C" shaped cross section rail member which opens downwardly and away from said underside of said brim structure; and eye wear structure attached to said attachment rail and displaceable along the length of said attachment rail, for providing eye protection to a wearer of said eye wear visor which may be adjusted closer to and farther away from said wearer and wherein said eye wear structure further comprises:

an attachment member having a cylindrical portion engaging the "C" shaped cross section rail member and an opening having a lateral axis displaced from an axis of said cylindrical portion;

a main longitudinal support extending through said opening;

a right lens assembly engaging said main longitudinal support on a first side of said attachment member; and a left lens assembly engaging said main longitudinal support on a second side of said attachment member.

2. The eye wear visor recited in claim 1 wherein said right lens assembly further comprises:

a right lens support structure having a bore engaging said main longitudinal support; and a right lens engaging said right lens support; and wherein said left lens assembly further comprises:

a left lens support structure having a bore engaging said main longitudinal support; and a left lens engaging said left lens support.

3. The eye wear visor recited in claim 2 wherein each of said right and left lenses have a pair "S" shaped interlock projections along their edges, and wherein said right and left lens supports have a complementary pair of "S" shaped interlock spaces for enabling the right and left lens supports to engage the right and left lenses, respectively.

4. The eye wear visor recited in claim 2 wherein each of said right and left lenses have a lower edge which sweeps rearwardly, and terminates in an acutely angled area.

5. The eye wear visor recited in claim 2 wherein said opening of said attachment member has an internal area which is partially hexagonally shaped, wherein said right and said left lens assemblies each have a bore, for engaging said main longitudinal support and wherein said main longitudinal support has an external hexagonal shape matching the internal shapes of said attachment member and said bores of said right and left lens assemblies.

6. An eye wear visor comprising:

a visor having a vertical curved wall and a sloping brim surface at the bottom of said curved wall, said brim surface having an underside, the structures of said visor having bilateral symmetry about a center line;

a first and a second lens lens support means, connecting said first and said second lens and said underside of said brim, for positioning said first lens and said second lens closer to and farther from each other and for moving said first lens and said second lens along the center line of said visor.

7. The eye wear visor recited in claim 6 wherein said lens support means is also for supporting said first and said second lens at a plurality of fixed angular positions with respect to said visor.

8. The eye wear visor recited in claim 7 wherein said lens support means further comprises:

an attachment rail attached to said underside of said visor structure;

an attachment member slidably attached to said attachment rail and an opening having a lateral axis displaced from an axis of said cylindrical portion;

a main longitudinal support extending through said opening;

a right lens assembly engaging said main longitudinal support on a first side of said attachment member; and a left lens assembly engaging said main longitudinal support on a second side of said attachment member.

9. The eye wear visor recited in claim 8 wherein said right lens assembly further comprises:

a right lens support structure having a bore engaging said main longitudinal support; and a right lens engaging said right lens support; and wherein said left lens assembly further comprises:

a left lens support structure having a bore engaging said main longitudinal support; and a left lens engaging said left lens support.

10. The eye wear visor recited in claim 9 wherein each of said right and left lenses have a pair of "S" shaped interlock projections along their edges, and wherein said right and left lens supports have a complementary pair of "S" shaped interlock spaces for enabling the right and left lens supports to engage the right and left lenses, respectively.

11. The eye wear visor recited in claim 9 wherein each of said right and left lenses have a lower edge which sweeps rearwardly, and terminates in an acutely angled area.

12. The eye wear visor recited in claim 8 wherein said opening of said attachment member has an internal area which is partially hexagonally shaped, wherein said right and said left lens assemblies each have a bore, for engaging said main longitudinal support wherein a main longitudinal support has an external hexagonal shape matching the internal shapes of said attachment member and said bores of said right and left lens assemblies.

* * * * *